United States Patent [19]

Merkel et al.

[11] 4,128,643
[45] Dec. 5, 1978

[54] 4-QUINAZOLINYL-GUANIDINES

[75] Inventors: Wulf Merkel, Bad Soden am Taunus; Hans G. Alpermann, Königstein, Taunus; Karl Geisen, Frankfurt am Main; Norbert Kothe, Kronberg, Taunus; Walter Ried, Frankfurt am Main, all of Fed. Rep. of Germany

[73] Assignee: Hoechst Aktiengesellschaft, Frankfurt am Main, Fed. Rep. of Germany

[21] Appl. No.: 800,918

[22] Filed: May 26, 1977

[30] Foreign Application Priority Data

May 28, 1976 [DE] Fed. Rep. of Germany ....... 2623846

[51] Int. Cl.² .................. C07D 413/04; A61K 31/505
[52] U.S. Cl. ............................... 424/251; 424/248.52;
424/248.56; 544/291; 544/249; 544/250;
260/243.3; 544/119; 544/115; 544/379;
544/403; 544/398; 544/377; 544/364; 544/360;
544/372; 544/394; 544/392; 544/165; 544/159;
544/141; 544/129; 544/148
[58] Field of Search ................ 544/119; 260/256.4 Q;
424/251, 248.52, 248.56

[56] References Cited

PUBLICATIONS

Ried et al. "Chem. Ber." 109 (1976) pp. 2706–2715.

*Primary Examiner*—Henry R. Jiles
*Assistant Examiner*—R. W. Ramsuer
*Attorney, Agent, or Firm*—Curtis, Morris & Safford

[57] ABSTRACT (2-Amino-4-quinazolinyl)-quanidines of the formula

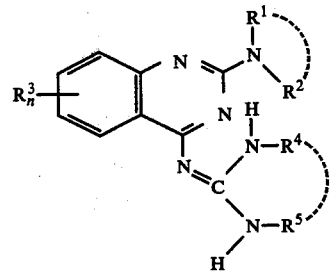

wherein $R^1$, $R^2$, $R^3$, $R^4$, $R^5$ and $n$ have the defined meanings, and their physiologically tolerable acid addition salts, process for preparing these compounds, pharmaceutical preparations containing them and their use as medicines.

6 Claims, No Drawings

4-QUINAZOLINYL-GUANIDINES

This invention relates to (2-amino-4-quinazolinyl)-guanidines of the formula I

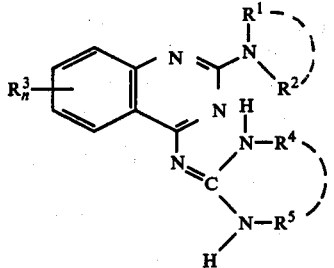

having valuable pharmacological properties, especially a blood-sugar reducing effect, in the free form as well as in the form of their physiologically tolerable acid addition salts.

In the formula
$R_1$ and $R_2$ represent
(a) each an alkyl group optionally substituted by an aromatic radical, a heterocyclic radical, or a cycloalkyl radical,
(b) each a cycloalkyl radical or
(c) together with the nitrogen atom a heterocyclic ring having from 3 to 8 members which may contain, besides the nitrogen, one or several hetero atoms selected from the group consisting of nitrogen, oxygen or sulfur, and which may be substituted at the nitrogen atom by an alkyl, a cycloalkyl, an aromatic, or an araliphatic radical, or
(d) one of the radicals $R^1$ or $R^2$ stands for a phenyl radical;
$R_3$ is hydrogen, halogen, $CF_3$, $CCl_3$, alkyl, alkoxy, or alkylthio each having from 1 to 3 carbon atoms, phenoxy, phenylthio, or phenyl, or dialkylamino having up to 8 carbon atoms altogether, piperidino, or pyrrolidino, an anellated aliphatic or aromatic ring or a methylene-dioxy group;
$R^4$ and $R^5$ each represent hydrogen, alkyl, cycloalkyl or benzyl or $R^4$ and $R^5$ together represent a bridge member having from 2 to 4 carbon atoms forming an optionally unsaturated 5 to 7 membered ring together with the two nitrogen atoms of the guanidine system; and
n is an integer in the range of from 1 to 4.

The substituents $R^1$ and $R^4$ can be identical or different. In the case of alkyl radicals they preferably have from 1 to 4 carbon atoms. As substituents for the alkyl radicals phenyl, thiophene and furane are preferred. The cycloalkyl radical is preferably cyclohexyl and cyclopentyl.

Especially preferred compounds of the formula I are those in which $R^1$ and $R^2$ form a heterocyclic 5 to 8 membered ring together with the nitrogen-atom.

Preferred examples of the grouping

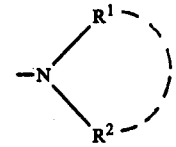

are aziridino-, azetidino-, pyrrolidino-, piperidino-, morpholino-, piperazino-, N-methylpiperazino-, N-benzyl-piperazino-, N-(2-thienylmethyl)-piperazino-, N-(2-furylmethyl)-piperazino-, N-(4-pyridylmethyl)-piperazino-, N-phenyl-piperazino-, N-(2-methoxyphenyl)-piperazino-, N-(2-chloro-phenyl)-piperazino-, N-(3-trifluormethylphenyl)-piperazino-, N-(3,4-dimethylphenyl)-piperazino-, N-(1-phenylethyl)-piperazino-, 1,2,3,4,-tetrahydro-isoquinolino-, diethylamino-, phenyl-methyl-amino-, dimethylamino-, dibutylamino-, dicyclohexylamino-, methylcyclohexyl-amino- and dibenzylamino-.

Further preferred compounds are those in which $R^3$ stands for hydrogen, alkyl, alkoxy, or alkylthio.

$R^4$ and $R^5$ preferably represent hydrogen or together an alkylene chain containing 2 or 3 methylene radicals.

n preferably stands for 1 or 2.

The invention also relates to processes for preparing compounds of formula I, pharmaceutical preparations containing or consisting of said compounds and their use in or as medicament(s).

The process of the invention is characterized in that
(a) a chloroformamidine of the formula II

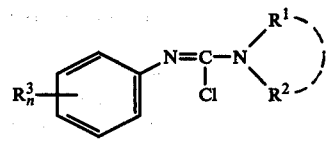

is reacted with a cyanoguanidine of the formula III

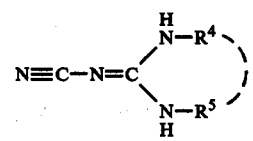

and the compound of formula I obtained is isolated in the form of the free base or as acid addition salt.

(b) a 4-quinazolylthio urea of formula V or the corresponding S-alkyl compound

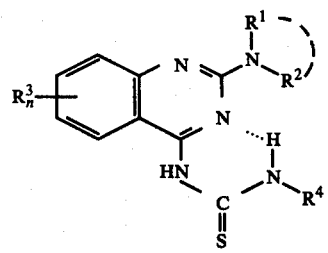

is reacted with an amine of formula $R^5$—$NH_2$ to give a compound of formula I in which $R^4$ and $R^5$ do not together form a bridge member;

(c) a 4-substituted quinazoline of formula VI

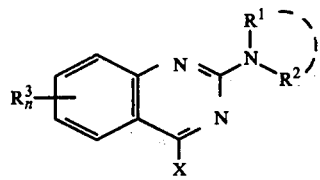

in which $R^1$ to $R^3$ have the indicated meanings and X can stand for halogen, S-alkyl, or S-aryl is reacted with a guanide of the formula VII

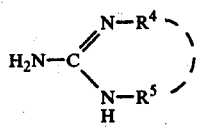

in which $R^4$ and $R^5$ have the indicated meanings by heating in mostly high boiling solvents.

(d) in a compound of formula I, in which $R^1$ and $R^2$ form together with the nitrogen atom a piperazine ring carrying in 4-position at the nitrogen atom a radical capable of being split off by hydrolysis or hydrogenolysis, said radical is split off and
the reaction products are optionally transformed into their physiologically tolerable acid addition salts.

The chloroformamidines of formula II are reacted with the cyanoguanidines of formula III in a proportion of from 1:1 to 1:4, preferably 1:2. The reaction takes place directly in the mixture or in an aprotic, absolute solvent, for example dimethoxyethane, tetrahydrofurane, acetonitrile, or dioxane, at room temperature or at elevated temperature up to the boiling point of the solvent used. The reaction mixture should be stirred thoroughly as the reaction is partly carried out in suspension. The 4-quinazolinyl-guanidines of formula I are mostly obtained as hydrochlorides and can be isolated as such or they remain in solution. By the addition of HCl the di- and possibly also the trihydrochloride of the corresponding quinazolinylguanidine are obtained, which are readily soluble in water. The free bases can be obtained from the acid addition salts by neutralization, for example with an alkali metal hydroxide, for example NaOH or KOH, or by adding triethylamine.

The starting compounds of formula II are prepared by processes known in the literature or by analogous methods (cf. for example H. Ulrich, The Chemistry of Imidoyl Halides, Plenum Press, New York, (1968); British Pat. No. 888,646 (1962); Chem. Abstracts 57, 1369e (1972); K. Itoh, A. Nozawa and Y. Ishii, Organometal. Chem. Syn. 1, 23 (1970/71); W. Ried und P. Weidemann, Chem. Ber. 104, 3329, (1971); W. Ried und W. Merkel, Chem. Ber. 105, 1532 (1972).

They are obtained, for example, by reacting a N-aryl-isocyano-dichloride with a secondary amine or an analogous derivative:

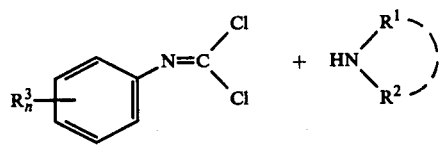

Another method consists of reacting a corresponding urea of formula IV with a chlorination agent.

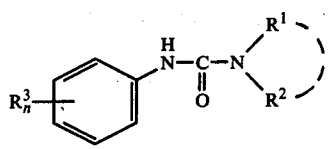

For this purpose, especially the process according to Appel (cf. R. Appel, K. D. Ziehm and K. Warning, Chem. Ber. 106, 2093 (1973); R. Appel, K. Warning and K. D. Ziehm, Chem. Ber. 107, 698 (1974)) can be used in a very broad sense.

A suitable chlorination reagent in this case is the system triphenyl phosphine/$CCl_4$, which is allowed to react with the urea at room temperature or slightly elevated temperature.

The chloroformamidines of formula II obtained can be used as starting material in the reaction with the cyanoguanidines III.

The 4-quinazolyl-thioureas, their S-methyl derivatives and the corresponding methoiodides and the preparation of said compounds are partly described in the literature (cf. W. Merkel, W. Ried, Chem Ber. 106, 471–483 (1973)).

In the direct reaction of an amine $R^5$—$NH_2$ with a thiourea V, in most cases a desulfurizing agent, for example a mercury or lead compound, is added to accelerate the reaction, whereby a carbodiimide is formed as intermediate product which directly adds the amine. The reaction of the S-alkyl compound V with $R^5$—$NH_2$ is brought about by heating in organic solvents.

The reaction according to (c) is carried out in usual manner, as known in the literature for analogous reactions, in a high boiling aprotic solvent, for example chlorobenzene or hexamethyl phosphoric acid trisamide.

The protective group is split off according to process (d) by methods known in the literature. Suitable protective groups are, for example, benzyl, furylmethyl or alkoxycarbonyl.

The novel compounds have valuable pharmacological properties, above all a hypoglycemic effect which may be accompanied by a diuretic effect or a hypotensive effect. They can also be used as valuable intermediates for the synthesis of pharmacologically effective compounds.

The novel compounds can be administered either per se or in admixture with pharmacologically tolerable carrier materials, oral administration being preferred. For this purpose, the active compounds are mixed with known substances and brought into a suitable form for administration by known methods, for example tablets, push-fit capsules, aqueous or oily suspensions, or aqueous or oily solutions. Suitable inert carrier materials are, for example, magnesium carbonate, milk sugar or cornstarch, with the addition of other substances, for example magnesium stearate. The medicinal preparations can be prepared in the form of dry or moist granules. Suitable oily carriers or solvents are especially vegetable or animal oils, for example sunflower oil or castor oil. The individual dose is in the range of from about 50 to 250 mg per tablet.

The novel compounds are especially suitable for mixing with other compounds. Besides other suitable substances, there are mentioned, above all:

antidiabetics such as glycodiazine, tolbutamide, glibenclamide, phenformin, buformin, and metformin; or circulatory preparations in the broad sense, in the first place coronary dilators such as chromonar or prenylamine; and hypoglycemic substances such as reserpine, α-methyl-dopa, or clonidine; lipid reducing substances; geriatric substances; pychopharmaceuticals, for example chlordiazepoxide, diazepam, or meprobamat; and vitamins.

The following examples illustrate the invention.

EXAMPLE 1

2-(2-pyrrolidino-4-quinazolinyl)-guanidine

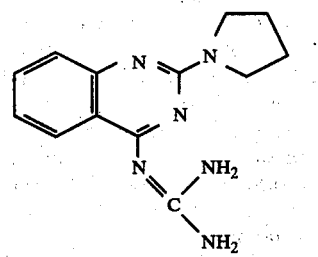

162 g of N-phenylcarbamoyl-pyrrolidine (prepared from phenyl isocyanate and pyrrolidine, melting point 133° C.) were dissolved in absolute acrylonitrile and 294 g of triphenyl phosphine and 85 ml CCl₄ were added. The mixture was stirred for 25 hours at room temperature, the solvent was distilled off and the reaction product extracted three times with dry ether. The formed triphenyl phosphine oxide precipitated and was separated from the ethereal solution. The combined ether extracts were concentrated and the remaining yellow chloroformamidine was used as crude product in the second reaction stage.

The chloroformamidine was stirred for 20 hours at room temperature in a proportion of 1:2 with 2 cyanoguanidine in absolute dimethoxyethane, whereby the hydrochloride of 2-(2-pyrrolidino-4-quinazolyl)-guanidine precipitated. It was filtered off, dissolved in $CH_3OH/H_2O$ and the free guanidine was precipitated by the addition of 2N NaOH. It was recrystallized from ethanol. The light yellow crystals melted at 265° C. and showed a light blue fluorescence in the range of 366 nm.

The di-hydrochloride was obtained by recrystallization from 2N HCl; decomposition range 305°–310° C.

Analysis $C_{13}H_{18}Cl_2N_6$ (329.2). Calculated: C 47.43 H 5.51 Cl 21.54 N 25.53. Found: C 47.1 H 5.4 Cl 21.6 N 25.2.

EXAMPLE 2

2-(2-N-methylpiperazino-4-quinazolinyl)-guanidine

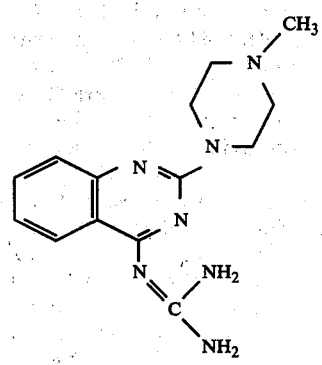

1 Mol of phenyl isocyanate was added dropwise while cooling to a solution of 1 mol of N-methyl-piperazine in 500 ml ethanol, upon which the solution warmed up. After the addition, stirring of the mixture was continued for about 30 minutes and the solution was concentrated. The remaining oil crystallized upon the addition of a small amount of water. The N-phenylcarbamoyl-4-methylpiperazine prepared in this manner and melting at 126°–127° C. (172 g) was dissolved in 1.9 l. absolute acetonitrile and 273 g of triphenyl phosphine and 80 ml CCl₄ were added while stirring. The mixture was stirred for 25 hours at room temperature, concentrated and the remaining oil was extracted with ether 3 to 5 times. The ethereal phases were combined and concentrated. The oily chloroformamidine obtained in this manner was directly dissolved in 750 ml absolute dimethoxyethane and stirred for 20 hours at room temperature together with 88 g of 2-cyanoguanidine. The precipitated product was filtered off and recrystallized from methanol with the addition of 2N HCl.

The di-hydrochloride of 2-(2-N-methylpiperazino-4-quinazolinyl)-guanidine obtained melted at 333°–334° C. with decomposition.

Analysis $C_{14}H_{21}Cl_2N_7$ (358.3). Calculated: C 46.93 H 5.91 Cl 19.79 N 27.36. Found: C 46.7 H 5.6 Cl 19.7 N 27.7.

EXAMPLE 3

(a) 2-(2-N-benzylpiperazino-4-quinazolinyl)-guanidine

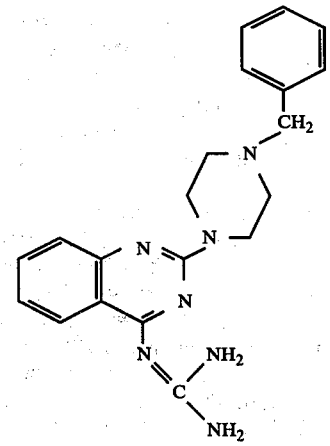

1 Mol of phenyl isocyanate were added dropwise while cooling to a solution of 1 mol of N-benzylpiperazine in 500 ml ethanol and the mixture was stirred for a further hour. The solution was a little concentrated whereby the "urea" crystallized out. By recrystallization from CH₃OH/H₂O the N-phenylcarbamoyl-4-benzyl-piperazine melting at 97°-98° C. was obtained.

176 Grams of this "urea" were dissolved in 1.6 l. absolute acetonitrile and 235 g triphenyl phosphine and 70 ml CCl₄ were added while stirring. The mixture was stirred for 25 hours at room temperature, concentrated and the remaining oil was extracted with absolute ether 3 to 5 times. The ethereal phases were combined and concentrated. The precipitating white chloroformamidine was immediately dissolved in 1 l absolute dimethoxyethane and 45 g of 2-cyanoguanidine were added while stirring. Stirring was continued for 20 hours at room temperature and for another 4 hours at 50° C. The precipitated product was filtered off with suction and recrystallized from CH₃OH with the addition of 2N HCl. The trihydrochloride of 2-(2-N-benzylpiperazino-4-quinazolinyl)-guandine obtained melted at 240°-244° C. with decomposition. It sintered approximately from 220° C. onward.

Analysis C₂₀H₂₆Cl₃N₇ (470.8). Calculated: C51.02 H 5.56 Cl 22.59 N 20.83. Found: C 51.4 H 5.9 Cl 20.4 N 21.6.

(b) By splitting off the benzyl group by catalytic hydrogenation in the presence of palladium/active carbon 2-(2-piperazino-4-quinazolinyl)-guanidine was obtained.

EXAMPLE 4

2-(6-Chloro-2-morpholino-4-quinazolinyl)-guanidine

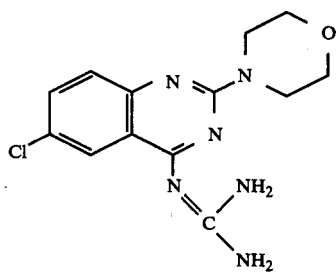

135 g of 4-(4-chlorophenylcarbamoyl)-morpholine were dissolved in 1 l absolute acetonitrile and 194 g of triphenylphosphine and 56 ml CCl₄ were added while stirring. The mixture was stirred for 20 hours at room temperature and for 5 hours at 50° C. with the exclusion of humidity, concentrated and the residue was thoroughly extracted with dry ether 3 to 5 times. The ether phases were combined and concentrated. The remaining solid matter was immediately dissolved in 1 l absolute dimethoxyethane and 106 g of 2-cyanoguanidine were added while stirring. Stirring was continued for 15 hours at room temperature and for 5 hours at 50° C. The precipitated product, which showed an intense blue-green fluorescence at 366 nm, was filtered off and recrystallized from 2N HV1. The dihydrochloride of 2-(6-chloro-2-morpholino-4-quinazolinyl)-guanidine obtained melted at 282°-283° C. with decomposition.

Analysis C₁₃H₁₇Cl₃N₆O (379.7). Calculated: C 41.12 H 4.51 Cl 28.01 N 22.13. Found: C 41.0 H 4.5 Cl 28.0 N 21.8.

Melting point of the monohydrochloride 272°-274° C. (decomposition). Melting point of the free base 230° C. with decomposition (contained 1 crystal water)

Example 5

2-(2-morpholino-4quinazolinyl)-guanidine

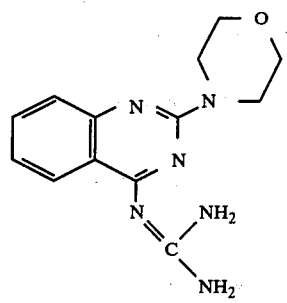

A solution of 0.2 mol morpholine in 300 ml absolute ether was slowly added dropwise, while thoroughly stirring, to 0.1 mol of phenyl isocyanide dichloride in about 300 ml absolute ether. The temperature was maintained between −10° and 0° C. Floculent morpholine hydrochloride precipitated. After filtration the ether was evaporated and the remaining yellowish white crystalline magma was boiled with about 200 to 300 ml n-hexane. The hot n-hexane solution was filtered. The chloroformamidine, i.e. morpholino-phenyliminomethyl chloride, crystallized on cooling in the form of long colorless needles melting at 65° C. 0.1 Mol of morpholino-phenyliminomethyl chloride and 0.2 mol of 2-cyanoguanidine were stirred for 20 hours at room temperature in absolute 1,2-dimethoxyethane, the precipitated hydrochloride of the quinazolinylguanidine was filtered off and recrystallized from CH₃OH. It melted at 284°-285° C.

The free 2-(2-morpholino-4-quinazolinyl)-guanidine was obtained by suspending the hydrochloride in CH₃OH and adding triethylamine, whereby the guanidine was dissolved. The methanol was distilled off and the free guanidine recrystallized from ethanol/H₂O. It melted at 197° C.

Analysis: hydrochloride C₁₃H₁₇ClN₆O (308.8). Calculated: C50.57 H 5.55 Cl 11.48 N 27.22. Found: C 50.4 H 5.5 Cl 11.6 N 27.0. Free guanidine C₁₃H₁₆N₆O (272,3). Calculated: C 57.34 H 5.92 N 30.86. Found: C 57.10 N 6.24 N 30.55.

EXAMPLE 6

2-(8-methyl-2-morpholino-4-quinazolinyl)-guanidine

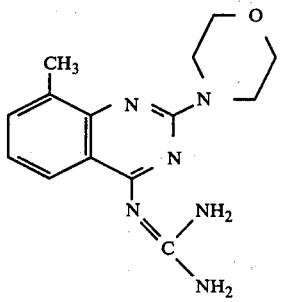

0.1 mol of the chloroformamidine morpholino-(2-methylphenylimino)-methyl chloride and 0.2 mol of 2-cyanoguanidine in absolute 1,2-dimethoxyethane were stirred for 20 hours at room temperature. The precipitated hydrochloride was filtered off and recrystallized from CH₃OH. It melted at 285°–287° C.

The free guanidine was prepared under the conditions specified in Example 5. After recystallization from ethanol/H₂O a colorless powder was obtained which melted at 222° C. with decomposition.

Analysis: hydrochloride $C_{14}H_{19}ClN_6O$ (322.8). Calculated C 52.09 H 5.89 N 26.05. Found C 52.33 H 5.89 N 26.17. free guanidine $C_{14}H_{18}N_6O$ (286.3) Calculated C 58.73 H 6.34 N 29.35. Found C 59.25 H 6.50 N 29.85.

EXAMPLE 7

2-(6-Phenyl-2-morpholino-4-quinazolinyl)-guanidine

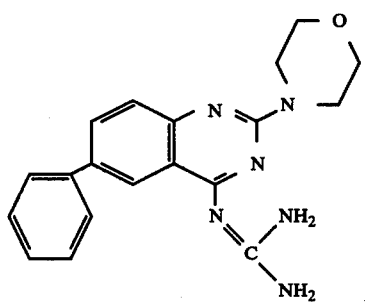

The compound was prepared under the conditions of Example 6 from morpholino-(4-phenylphenylimino)-methyl chloride. Hydrochloride melting point: 251°–257° C., free guanidine melting point: 248° C. with decomposition; it contained 1 crystal ethanol when recrystallized from ethanol.

Analysis: hydrochloride $C_{19}H_{21}ClN_6O$ (384.9). Calculated C 59.30 H 5.50 N 21.84. Found C 58.99 H 5.60 N 21.54.

EXAMPLE 8

2-(2-morpholinobenzo[h]-quinazolin-4-yl)-guanidine

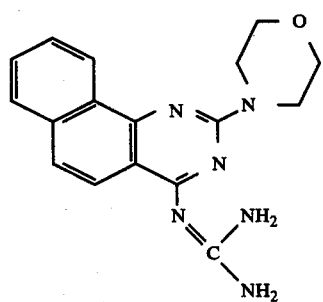

The compound was prepared under the conditions of Example 6 from morpholino-α-naphthyliminomethyl chloride. Hydrochloride melting point: 316° C. with decomposition free quanidine melting point: 235° C. with decomposition, colorless needles when recrystallized from CH₃OH.

Analysis: hydrochloride $C_{17}H_{19}ClN_6O$ (358.8). Calculated C 56.90 H 5.34 N 23.42. Found C 55.56 H 5.47 N 22.78. Free guanidine $C_{17}H_{18}N_6O$. Calculated C 63.34 H 5.63 N 26.07. Found C 62.52 H 5.77 N 25.24.

EXAMPLE 9

Aniline-carboxylic acid-(4)-amide-[2-morpholino-quinazolinyl-(4)-imine]

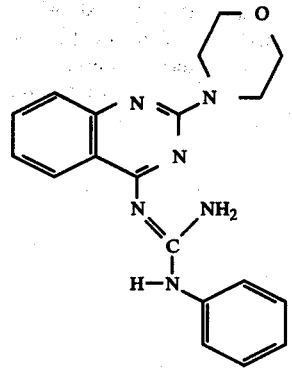

Equivalent amounts of thiocarbonic acid anilide -(2-morpholino-4-quinazolyl-amide) and a mercury compound (HgO or Hg (C≡C—C₆H₅)₂) were dissolved or suspended in absolute dioxane and dry gaseous NH₃ was introduced. The mixture was refluxed while thoroughly stirring, whereupon black HgS precipitated. After having refluxed for about 1 hour, the mixture was filtered and the strongly fluorescent solution was concentrated by evaporation. The remaining oil was taken up in chloroform and the solution was cautiously covered with a layer of n-hexane. The reaction product crystallized with 1 mol of crystal chloroform It melted at 99°–100° C.

Analysis $C_{19}H_{20}N_6O \cdot HCl$ (467.8). Calculated C 51.56 H 4.52 N 17.96. Found C 51.05 H 4.50 N 17.70.

The product could also be recrystallized from benzene. It melted at 99°–100° C.

Analysis $C_{19}H_{20}N_6O \cdot C_6H_5$ (426.5). Calculated C 70.40 H 6.14 N 19.70. Found C 70.45 H 6.04 N 10.66.

What is claimed is:

1. A (2-amino-4-quinazolinyl)-guanidine of the formula

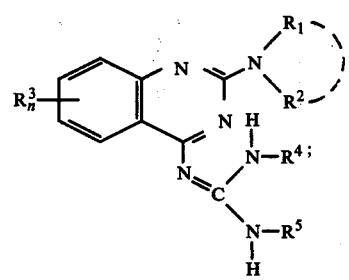

and physiologically tolerable acid addition salts thereof wherein $R^1$ and $R^2$, taken together with the nitrogen atom to which they are attached, are morpholino, N-methyl piperazino, N-benzylpiperazino, piperidins, or pyrrolidino;

$R^3$ is hydrogen, halogen, —CF₃, —CCl₃, alkyl alkoxy, alkylthio, each having from 1 to 3 carbon atoms phenoxy, phenyl, phenylthio, or dialkylamino having up to 8 carbon atoms altogether and n is an integer from 1 to 4, or $R_3$ is a fused benzo group; and $R^4$ and $R^5$ are hydrogen, alkyl having 1 to 4 carbon atoms, cyclopentyl, cyclohexyl, or benzyl.

2. A compound as in claim 1 wherein $R^4$ and $R^5$ are hydrogen.

3. A compound as in claim 1 which is 2-(2-N-methyl-piperazino-4-quinazolinyl)-guanidine.

4. A compound as in claim 1 which is 2-(2-N-benzyl-piperazino-4-quinazolinyl)-guanidine.

5. A hypoglycemic composition comprising an inert pharmaceutical carrier and a hypoglycemically-effective amount of a compound as in claim 4.

6. The method of treating hyperglycemia in a patient suffering therefrom which comprises orally administering to said patient a hypoglycemically-effective amount of a compound as in claim 4.

* * * * *